United States Patent
Hatcher, Jr. et al.

(10) Patent No.: US 9,988,925 B2
(45) Date of Patent: *Jun. 5, 2018

(54) LASER MEASUREMENT SYSTEM FOR DETECTING TURBINE BLADE LOCKUP

(71) Applicant: Siemens Energy, Inc., Orlando, FL (US)

(72) Inventors: Clifford Hatcher, Jr., Orlando, FL (US); Forrest R. Ruhge, Orlando, FL (US)

(73) Assignee: SIEMENS ENERGY, INC., Orlando, FL (US)

( * ) Notice: Subject to any disclaimer, the term of this patent is extended or adjusted under 35 U.S.C. 154(b) by 441 days.

This patent is subject to a terminal disclaimer.

(21) Appl. No.: 14/576,747

(22) Filed: Dec. 19, 2014

(65) Prior Publication Data

US 2016/0177771 A1    Jun. 23, 2016

(51) Int. Cl.
| | |
|---|---|
| *F01D 17/06* | (2006.01) |
| *F01D 5/30* | (2006.01) |
| *F01D 21/00* | (2006.01) |
| *F01D 17/02* | (2006.01) |
| *G01M 1/00* | (2006.01) |
| *G01N 21/88* | (2006.01) |
| *G01N 21/954* | (2006.01) |

(52) U.S. Cl.
CPC ............... *F01D 17/06* (2013.01); *F01D 5/30* (2013.01); *F01D 17/02* (2013.01); *F01D 21/003* (2013.01); *F05D 2220/36* (2013.01); *F05D 2220/74* (2013.01); *F05D 2260/80* (2013.01); *F05D 2260/83* (2013.01); *F05D 2270/02* (2013.01); *G01M 1/00* (2013.01); *G01N 21/88* (2013.01); *G01N 2021/9546* (2013.01)

(58) Field of Classification Search
CPC ........ F01D 17/06; F01D 11/006; G01M 1/00; F05D 2260/83; G01N 2021/9546
See application file for complete search history.

(56) References Cited

U.S. PATENT DOCUMENTS

| | | | | |
|---|---|---|---|---|
| 4,413,519 A | * | 11/1983 | Bannister | G01S 13/88 342/118 |
| 4,572,663 A | * | 2/1986 | Greene | F01D 21/003 348/132 |

(Continued)

FOREIGN PATENT DOCUMENTS

| | | | | |
|---|---|---|---|---|
| CN | 203838341 | * | 9/2014 | G01S 17/08 |

*Primary Examiner* — Manish S Shah
*Assistant Examiner* — Timothy Graves

(57) ABSTRACT

A laser measurement system for detecting at least one locked blade assembly in a gas turbine. The system includes at least one laser device for emitting a laser beam that impinges on a blade surface of each blade in a row of blade assemblies. The laser beam is also transmitted through a space between adjacent blades to impinge on corresponding internal surfaces of the gas turbine. Further, the system includes a photon detector for detecting a first time period in which first laser energy is reflected from each blade surface and a second time period in which second laser energy is reflected from each internal surface and transmitted through each space. The system also includes a controller for detecting a change in at least one second time period to indicate that a distance between consecutive blades has changed and that at least one locked blade assembly is locked.

20 Claims, 4 Drawing Sheets

(56) References Cited

U.S. PATENT DOCUMENTS

| | | | | |
|---|---|---|---|---|
| 5,095,252 A | * | 3/1992 | Kurth | H05B 41/34 315/200 A |
| 6,992,315 B2 | * | 1/2006 | Twerdochlib | F01D 5/005 250/330 |
| 2007/0132461 A1 | * | 6/2007 | Holmquist | F01D 17/02 324/644 |
| 2013/0115050 A1 | * | 5/2013 | Twerdochlib | F01D 21/14 415/118 |

* cited by examiner

LASER MEASUREMENT SYSTEM FOR DETECTING TURBINE BLADE LOCKUP

CROSS-REFERENCE TO RELATED APPLICATION

The entire disclosure of U.S. application Ser. No. 14/576,919, filed on the same day herewith, entitled OPTICAL MEASUREMENT SYSTEM FOR DETECTING TURBINE BLADE LOCKUP and having inventors Forrest R. Ruhge and Clifford Hatcher, Jr., is incorporated by reference in its entirety.

FIELD OF THE INVENTION

This invention relates to the detection of locked blade assemblies in a gas turbine, and more particularly, to a laser measurement system that includes at least one laser device for emitting a laser beam, a photon detector for detecting respective time periods for first laser energy reflected from turbine blades and second laser energy reflected from internal surfaces of the gas turbine and transmitted through spaces between the blades, and a controller for detecting a change in a time period indicating that a distance between consecutive blades has changed thereby indicating at least one locked blade assembly.

BACKGROUND OF THE INVENTION

In various multistage turbomachines used for energy conversion, such as gas turbines, a fluid is used to produce rotational motion. Referring to FIG. 1, an axial flow gas turbine 10 includes a compressor section 12, a combustion section 14 and a turbine section 16 arranged along a horizontal center axis 17. The compressor section 14 provides a compressed air flow to the combustion section 14 where the air is mixed with a fuel, such as natural gas, and ignited to create a hot working gas. The turbine section 16 includes a plurality of blade assemblies 20 arranged in a plurality of rows. The hot gas expands through the turbine section 16 where it is directed across the rows of blade assemblies 20 by associated stationary vanes 22. The blade assemblies 20 are ultimately attached to a shaft that is rotatable about the center axis 17. As the hot gas passes through the turbine section 16, it causes the blade assemblies 20 and thus the shaft to rotate, thereby providing mechanical work. Each row of blade assemblies 20 and associated vanes 22 form a stage. In particular, the turbine section 16 may include four rows of blade assemblies 20 and associated vanes 22 to form four stages. The gas turbine 10 further includes an exhaust cylinder section 18 located adjacent the turbine section 16 and an outer diffuser section 24 located adjacent the exhaust cylinder section 18.

Many gas turbines may utilize a portion of the compressed air generated by the compressor section 12 as a cooling fluid for cooling hot components of the combustion 14 and turbine sections 16 of the gas turbine 10. In one type of cooling system design known as a closed loop cooling system, a seal pin arrangement is used to form a seal between adjacent rotating blade assemblies 20. FIG. 2 illustrates an exemplary rotatable blade assembly 20 used in the gas turbine 10. Blade assembly 20 includes a root section 26 that is attached to a rotor and a platform section 28 that extends from the root section 26. An airfoil or turbine blade 30 extends from the platform 28 on an opposite side from the root section 26. The platforms 28 are located on the rotor such that each blade 30 is substantially evenly spaced from an adjacent blade 30. The blade 30 extracts heat and pressure energy from the hot gas as it passes over the blade assembly 20 and converts the energy into mechanical energy by rotating the shaft.

The platform 28 is sealed and damped against a corresponding platform 28 of an adjoining blade assembly 20 by seal pins 32 and 34. The pins 32 and 34 are positioned in corresponding pin slots 36 and 38 formed into a surface 40 of the platform 28. The pin slots 36 and 38 are arranged such that centrifugal force generated by rotation about the center axis 17 loads the pins 32 and 34. This forces the pins 32 and 34 out of a resting position in the pin slots 36 and 38 so that the pins 32 and 34 are urged against a corresponding surface of a platform 28 of an adjoining blade assembly 20, thereby forming a seal and damping structure.

SUMMARY OF INVENTION

A laser measurement system is disclosed for detecting at least one locked blade assembly in a gas turbine having a plurality of blade assemblies arranged in rows wherein each blade assembly includes a blade and adjacent blades in a row are separated by a first distance forming a space between adjacent blades. The system includes at least one laser device for emitting a laser beam that impinges on a blade surface of each blade in a row of blades. Further, the laser beam is also transmitted through a space between adjacent blades to impinge on corresponding internal surfaces of the gas turbine. The system further includes a photon detector for detecting a first time period in which first laser energy is reflected from each blade surface and a second time period in which second laser energy is reflected from each internal surface and transmitted through each space to provide a plurality of first and second time periods. Further, the system includes a controller for controlling operation of the laser device and photon detector. In particular, detection of a change in at least one second time period relative to remaining second time periods indicates that a distance between consecutive blades has changed relative to the first distance thereby indicating at least one locked blade assembly.

Further, a method is disclosed for detecting at least one locked blade assembly in a gas turbine having a plurality of blade assemblies arranged in rows wherein each blade assembly includes a blade and wherein adjacent blades in a row are separated by a first distance forming a space between adjacent blades. The method includes emitting a laser beam that impinges on a blade surface of each blade in a row of blades located adjacent an exhaust cylinder section of the gas turbine. Further, the laser beam is also transmitted through each space between adjacent blades to impinge on corresponding internal surfaces of the gas turbine. The method further includes detecting a first time period in which first laser energy is reflected from each blade surface and a second time period in which second laser energy is reflected from each internal surface and transmitted through each space to provide a plurality of first and second time periods. Further, the method includes detecting whether at least one second time period has increased relative to remaining second time periods wherein an increase in at least one second time period indicates that a distance between consecutive blades has increased relative to the first distance thereby indicating at least one locked blade assembly.

Those skilled in the art may apply the respective features of the present disclosure jointly or severally in any combination or sub-combination.

BRIEF DESCRIPTION OF DRAWINGS

The teachings of the present disclosure can be readily understood by considering the following detailed description in conjunction with the accompanying drawings, in which.

To facilitate understanding, identical reference numerals have been used, where possible, to designate identical elements that are common to the figures.

DETAILED DESCRIPTION

Figure 1:
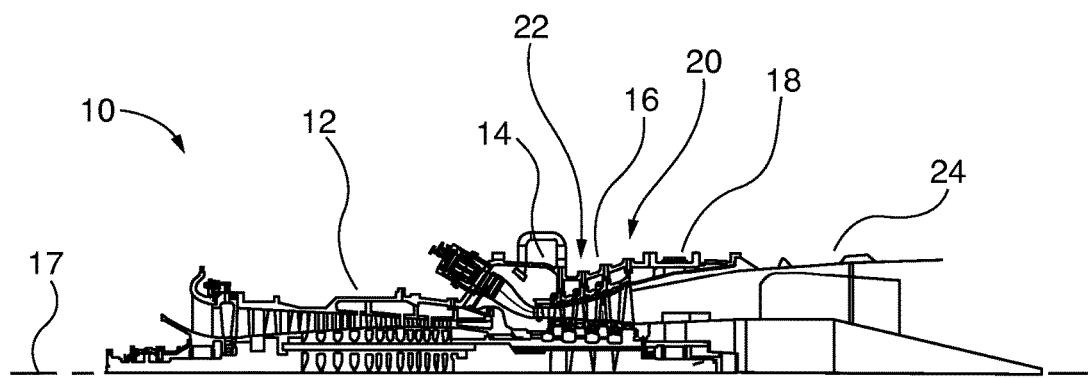
FIG. 1 is a partial view an axial flow gas turbine.
Figure 2:
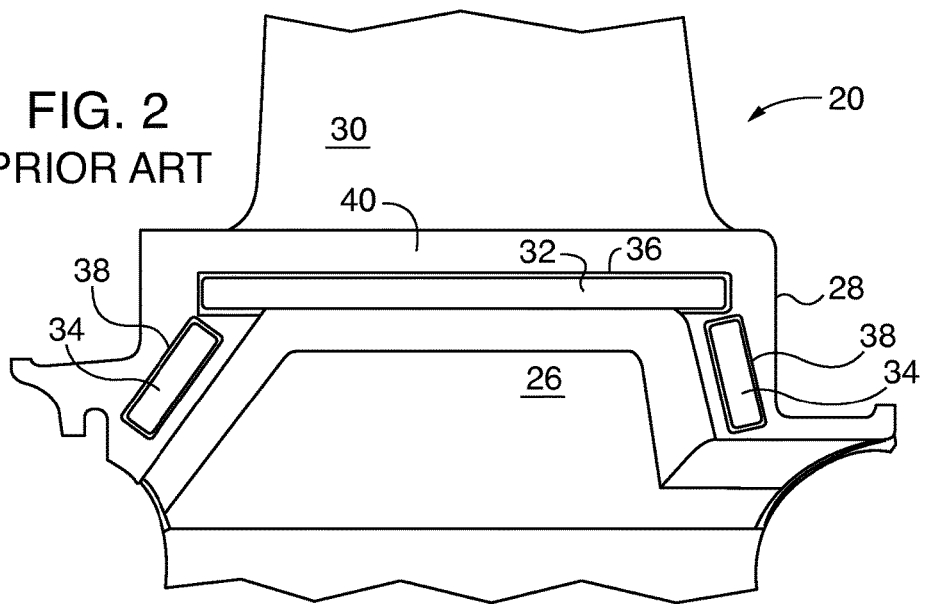
FIG. 2 is a view of an exemplary rotatable blade assembly used in the gas turbine.

Although various embodiments that incorporate the teachings of the present disclosure have been shown and described in detail herein, those skilled in the art can readily devise many other varied embodiments that still incorporate these teachings. The scope of the disclosure is not limited in its application to the exemplary embodiment details of construction and the arrangement of components set forth in the description or illustrated in the drawings. The disclosure encompasses other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

It has been found by the inventors herein that at least one seal pin 32, 34 associated with at least one blade assembly 20 of the turbine section 16 may migrate from an associated pin slot 36, 38 and become undesirably wedged between adjoining or consecutive platforms 28. Pin migration may occur during a known turning gear operation wherein a turning gear mechanism is used to slowly rotate a turbine shaft prior to startup of a cold gas turbine 10 or after shutdown of the gas turbine 10 to remove or inhibit sagging of the shaft. During a turning gear operation, the shaft rotates at a turning gear speed (for example, approximately 3 to 5 rpm) that is substantially less than normal turbine operating speed (for example, approximately 3600 rpm). This results in the generation of a substantially reduced centrifugal force that in turn sufficiently unloads the seal pins 32, 34 such that at least one pin 32, 34 becomes loose, migrates out of its associated slot 36, 38 and ultimately becomes wedged in between adjoining platforms 28. When a seal pin 32, 34 is wedged between adjoining platforms 28, an operational frequency and/or vibration characteristic of the blade 30 is changed that results in an undesirable increase in mechanical stress exerted on the blade 30 at a location near the platform 28.

The unloading of the pins 32, 34 due to reduced rotational speed during a turning gear operation also results in each blade assembly 20 being loosely attached to its corresponding rotor. As a result, each blade assembly 20 is able to shift or move as it is rotated about the center axis 17. When a pin 32, 34 becomes wedged between adjoining platforms 28, movement of the adjoining blade assemblies 20 is inhibited and the adjoining blade assemblies 20 become immobilized, i.e. the blades assemblies 20 are locked. Further, the wedged pin 32, 34 displaces the adjoining platforms 28 away from each other such that a distance between corresponding consecutive locked blades 30 is increased, thus resulting in unevenly spaced blades 30 in a row of blades 30. Further, displacement of the adjoining platforms 28 away from each other also decreases the distance between a locked blade 30 and an adjacent unlocked blade 30.

Figure 3:
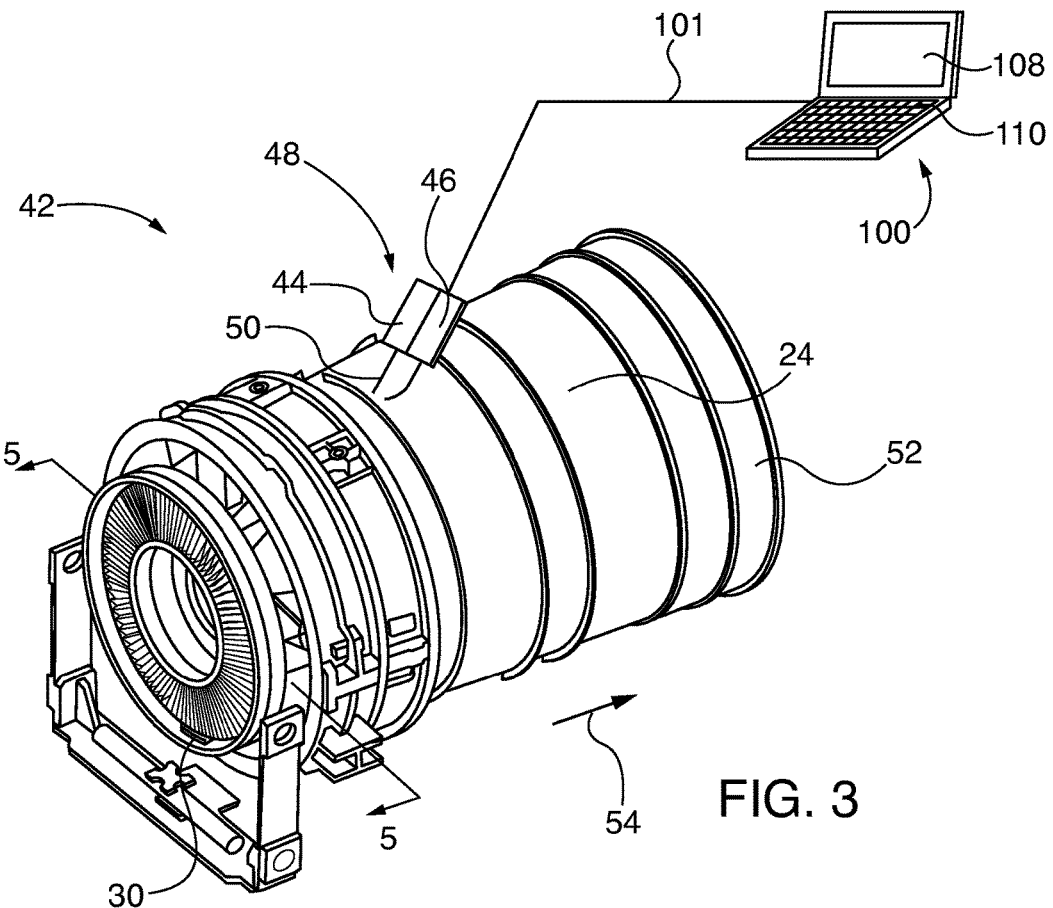
FIG. 3 is a schematic of a laser measurement system for detection of blade lockup of consecutive blade assemblies.
Figure 4:
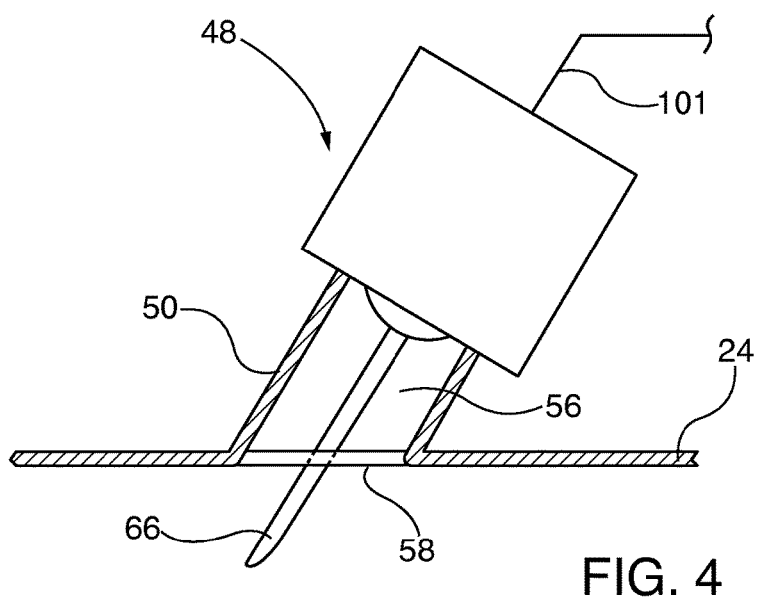
FIG. 4 is a partial cross sectional view of a port shown in FIG. 3.

Referring to FIG. 3, a laser measurement system 42 for detection of blade lockup is shown. Although the current disclosure discusses blade lockup in a gas turbine, it is understood that the current disclosure is applicable to other types of turbine engines that experience blade lockup. The system 42 includes a known laser device 44 and a known photon detector 46 which together form a laser module 48. In an alternate embodiment, the photon detector 46 may be located separately from the laser device 44. In yet another embodiment, a laser rangefinder may be used. The laser module 48 is attached to an angled port 50 located on a surface 52 of the gas turbine 10 such as the outer diffuser 24, although it is understood that other surface locations may be used. Arrow 54 depicts a direction of exhaust flow in the outer diffuser 24. Referring to FIG. 4, a partial cross sectional view of the port 50 is shown. The port 50 may be preexisting port or a new port thrilled in the outer diffuser 24. The port 50 includes a through hole 56 and a lens 58 fabricated from sapphire glass that forms part of the outer diffuser 24. In an alternate embodiment, a plurality of laser modules 48 and associated ports 50 may be used. For example, the laser modules 48 and associated ports 50 may be located in a circumferential and/or staggered arrangement around the outer diffuser 24.

Figure 5:
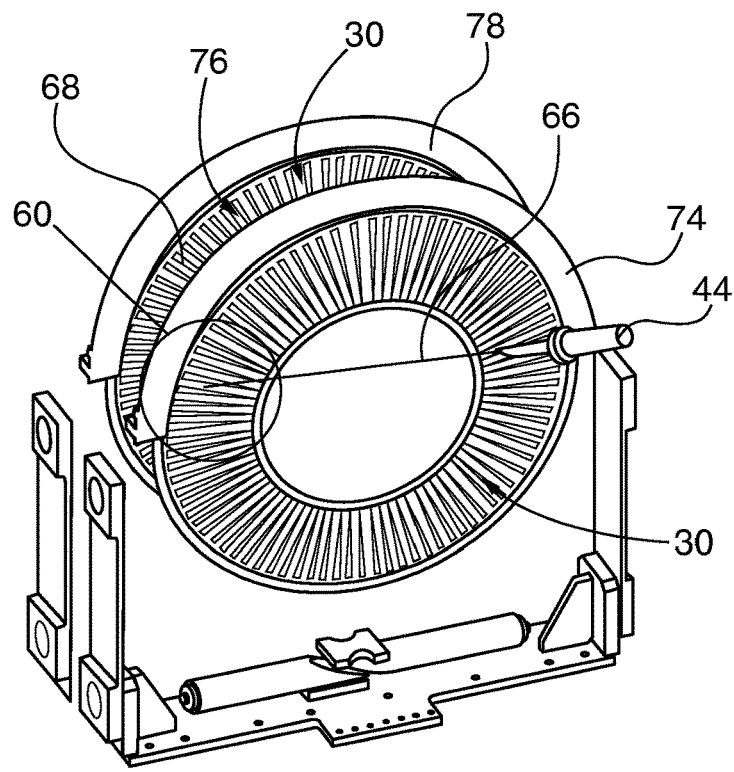
FIG. 5 is a view of a row of blades along view line 5-5 of FIG. 3.
Figure 6:
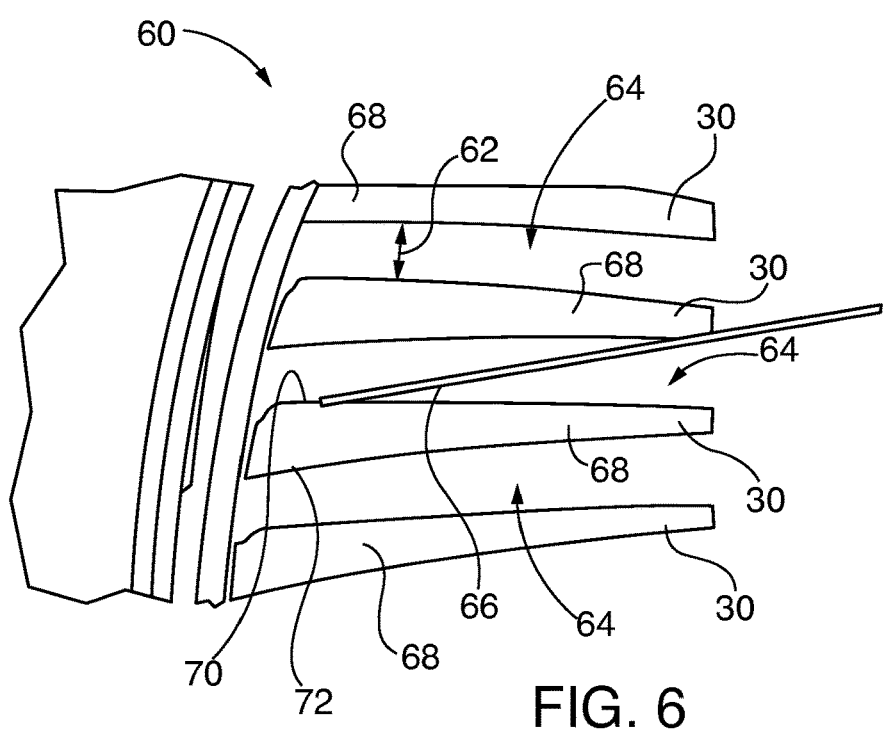
FIG. 6 is an enlarged view of balloon section 60 of FIG. 5.

Referring to FIG. 5, a view of a row of blades 30 along view line 5-5 of FIG. 3 is shown. Referring to FIG. 6, an enlarged view of balloon section 60 of FIG. 5 is shown. When adjoining blade assemblies 20 are not locked (i.e. When pins 32, 34 are not wedged between adjoining platforms 28), each blade 30 is separated by a first distance 62 from an adjacent blade 30 thereby forming an evenly spaced blade arrangement Wherein each blade 30 is separated from an adjacent blade 30 by a space 64. Referring to FIGS. 3-6, the laser device 44 emits a laser beam 66 that is transmitted through the hole 56 and lens 58 and impinges on a blade surface 68 of each blade 30 as the blades 30 rotate about the center axis 17. For example, the laser beam 66 may impinge on a blade surface 68 extending between a trailing edge 70 and a leading edge 72 of each blade 30. In an embodiment, the port 50 is oriented such that the laser beam 66 impinges on each blade 30 of a row of blades 30 located adjacent the exhaust cylinder section 18, such as a fourth row 74 of blades 30 of a four stage turbine section 16. It is understood that the laser beam 66 may be oriented such that it impinges on other rows of blades 30 of the turbine section 16.

The laser beam 66 is also transmitted through the spaces 64 between the blades 30 and impinges on internal surfaces 76 of the gas turbine 10 that are located behind the blades 30 and correspond to the spaces 64. By way of example, the internal surfaces 76 may be a blade surface 68 of at least one blade 30 located in a row 78 of blades 30 adjacent to the fourth row 74 of blades 30 and/or its associated components.

The laser beam 66 is then reflected from each blade surface 68 of each blade 30 in the fourth row 74. The laser beam 66 is also reflected from each internal surface 76 and is transmitted through each space 64. The reflected laser beam 66 is also transmitted through the lens 58 and hole 56 to ultimately impinge on the photon detector 46. The internal surface 76 corresponding to each space 64 is located further away from the photon detector 46 than the blade surface 68 of each blade 30 in the fourth row 74. Thus, an intensity of laser energy reflected from an internal surface 76 is substantially less than an intensity reflected from the blade 30.

Figure 7:
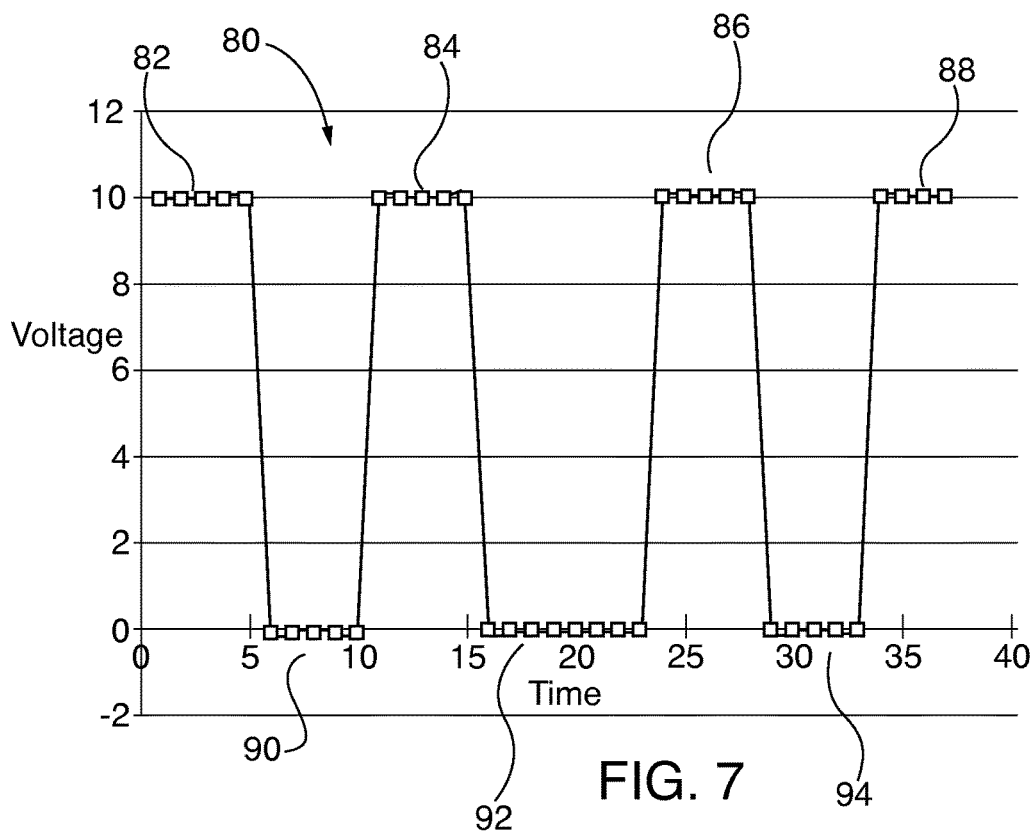
FIG. 7 depicts an exemplary simulated graph of laser energy intensity reflected from selected blade surfaces, and internal surfaces corresponding to spaces between the blades, during a single rotation of a fourth row of blades about a center axis.

Referring to FIG. 7, an exemplary simulated graph 80 is shown which depicts laser energy intensity (measured in volts along y-axis) reflected from blade surfaces 68, and internal surfaces 76 corresponding to spaces 64, during a single rotation of a fourth row 74 of blades 30 about the center axis 17. Regions 82, 84, 86, 88 each have a higher voltage and thus energy intensity than regions 90, 92, 94 thus indicating that regions 82, 84, 86, 88 each correspond to laser energy reflected from a blade surface 68 of each blade 30. Accordingly, regions 90, 92, 94 each correspond to laser energy reflected from an internal surface and transmitted through a corresponding space 64. A time period associated with each region 82, 84, 86, 88 and 90, 92, 94 is shown on the x-axis in FIG. 7.

The time period for region 92 is greater than the time period for either regions 90 or 94, thus indicating that laser energy is reflected from an internal surface for a longer period of time in region 92 than in either regions 90 or 94. As previously described, a locked blade assembly 20 increases the distance between corresponding consecutive locked blades 30. In particular, the distance is increased to a distance greater than the first distance 62. In accordance with embodiments of the invention, an increase in the period of time in which laser energy is reflected from an internal surface 76 corresponding to a space 64, such as shown in region 92, indicates that a distance between consecutive blades 30 has increased beyond the first distance 62. This in turn indicates that a blade assembly pair 20 has undesirably locked. Further, the time periods for regions 90 and 94 are substantially equal to each other, thus indicating that the associated blade assemblies 20 for regions 90 and 94 are not locked. It is understood that the graph 80 may include more than one region having a time period that is greater than the time periods for regions 90 or 94 and having a similar voltage as regions 90 or 94, thus indicating more than one locked blade assembly 20. Further, the graph 80 may depict at least one region having a shorter time period than the time period for either regions 90 or 94 and having a similar voltage as regions 90 or 94. This indicates a decrease in the distance between consecutive blades 30 such as between an unlocked blade 30 and an adjacent locked blade 30. In an embodiment, a baseline dataset is first obtained for a row of blades that does not have locked blade assemblies. A wedged dataset is then obtained for a row of blades 30 that has at least one locked blade assembly pair 20. The baseline dataset is then subtracted from the wedged dataset to indicate the existence of at least one locked blade assembly 20 to an operator.

Figure 8:
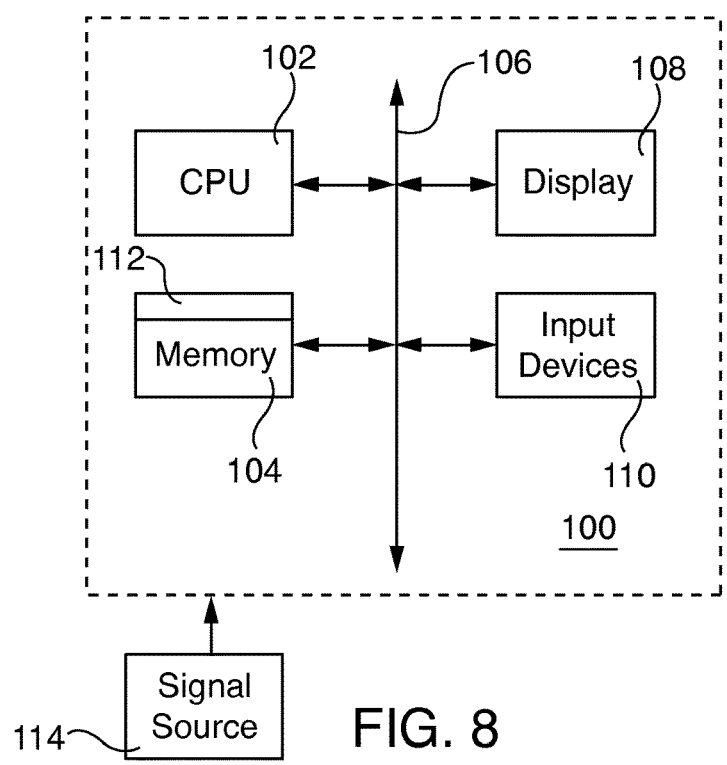
FIG. 8 is a block diagram of a computer.

Referring back to FIG. 3, the system 42 also includes a computer 100 that is coupled to the laser module 48 using a known technique such as a fiber optic cable 101 or alternatively a known wireless technique may be used. The computer 100 includes software and drivers that enable the computer 100 to serve as controller for controlling operation of the laser device 44 and photon detector 46 and to process, visualize and store measurement data. The computer 100 may use well-known computer processors, memory units, storage devices, computer software, and other components. A high level block diagram of such a computer 100 is illustrated in FIG. 8. Computer 100 may include a central processing unit (CPU) 102, a memory 104 and an input/output (I/O) interface 106. The computer 100 is generally coupled through the I/O interface 106 to a display 108 for visualization and various input devices 110 that enable user interaction with the computer 100 such as a keyboard, keypad, touchpad, touchscreen, mouse, speakers, buttons or any combination thereof. Support circuits may include circuits such as cache, power supplies, clock circuits, and a communications bus. The memory 104 may include random access memory (RAM), read only memory (ROM), disk drive, tape drive, etc., or a combination thereof. Embodiments of the present invention may be implemented as a routine 112 that is stored in memory 104 and executed by the CPU 102 to process the signal from a signal source 114. As such, the computer 100 is a general purpose computer system that becomes a specific purpose computer system when executing the routine 112. The computer 100 can communicate with one or more networks such as a local area network (LAN), a general wide area network (WAN), and/or a public network (e.g., the Internet) via a network adapter. One skilled in the art will recognize that an implementation of an actual computer could contain other components as well, and that FIG. 8 is a high level representation of some of the components of such a computer for illustrative purposes.

The computer 100 also includes an operating system and micro-instruction code. The various processes and functions described herein may either be part of the micro-instruction code or part of the application program (or a combination thereof) which is executed via the operating system. In addition, various other peripheral devices may be connected to the computer platform such as an additional data storage device and a printing device. Examples of well-known computing systems, environments, and/or configurations that may be suitable for use with computer 88 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

It is to be understood that exemplary embodiments of the present invention may be implemented in various forms of hardware, software, firmware, special purpose processors, or a combination thereof. In one embodiment, aspects of the current disclosure may be implemented in software as an application program tangibly embodied on a computer readable storage medium or computer program product. As such, the application program is embodied on a non-transitory tangible media. The application program may be uploaded to, and executed by, a processor comprising any suitable architecture.

Aspects of the current invention may be used during a turning gear operation in order to indicate that a seal pin 32, 34 has become wedged between a pair of blade assemblies 20. A visual inspection of the turning blade assemblies 20 may then be conducted. This significantly reduces inspection time relative to the current process that is being used. In addition, the system 42 may be installed at a customer site at minimal cost.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A laser measurement system for detecting at least one locked blade assembly that becomes locked during a turning gear operation for a gas turbine wherein the gas turbine includes a plurality of blade assemblies arranged in rows wherein each blade assembly includes a blade and wherein adjacent blades in a row are separated by a first distance forming a space between adjacent blades to orient each blade in a first position, comprising:
   at least one laser device for emitting a laser beam that impinges on a blade surface of each blade in a row of blades and wherein the laser beam is also transmitted through each space between adjacent blades to impinge on corresponding internal surfaces of the gas turbine;
   a photon detector for detecting a first time period in which first laser energy is reflected from each blade surface and a second time period in which second laser energy is reflected from each internal surface and transmitted through each space to provide a plurality of first and second time periods; and
   a controller for controlling operation of the laser device and photon detector wherein the first distance is measured from a first blade that is not deflected from the first position during the turning gear operation and detection of a change in at least one second time period relative to remaining second time periods indicates that a distance between the first blade and an adjacent blade has changed relative to the first distance thereby indicating at least one locked blade assembly.

2. The system according to claim 1, wherein the change in at least one second time period includes an increase in the time period.

3. The system according to claim 1, wherein the change in at least one second time period includes a decrease in the time period.

4. The system according to claim 1, wherein an intensity of the first laser energy is greater than an intensity of the second laser energy.

5. The system according to claim 1, wherein the blade surface extends between a trailing edge and a leading edge of each blade.

6. The system according to claim 1, wherein the laser device and photon detector are included in a laser module.

7. The system according to claim 6, wherein the gas turbine includes a port and the laser module is attached to the port.

8. The system according to claim 7, wherein the port is located on an outer diffuser of the gas turbine.

9. The system according to claim 7, wherein the port is oriented such that the laser beam impinges on a row of blades located adjacent an exhaust cylinder section of the gas turbine.

10. A method for detecting at least one locked blade assembly that becomes locked during a turning gear operation for a gas turbine wherein the gas turbine includes a plurality of blade assemblies arranged in rows wherein each blade assembly includes a blade and wherein adjacent blades in a row are separated by a first distance forming a space between adjacent blades to orient each blade in a first position, comprising:
   emitting a laser beam that impinges on a blade surface of each blade in a row of blades and wherein the laser beam is also transmitted through each space between adjacent blades to impinge on corresponding internal surfaces of the gas turbine;
   detecting a first time period in which first laser energy is reflected from each blade surface and a second time period in which second laser energy is reflected from each internal surface and transmitted through each space to provide a plurality of first and second time periods; and
   detecting whether a change has occurred in at least one second time period relative to remaining second time periods wherein the first distance is measured from a first blade that is not deflected from the first position during the turning gear operation and detection of a change in at least one second time period indicates that a distance between the first blade and an adjacent blade has changed relative to the first distance thereby indicating at least one locked blade assembly.

11. The method according to claim 10, wherein the change in at least one second time period includes an increase in the time period.

12. The method according to claim 10, wherein the change in at least one second time period includes a decrease in the time period.

13. The method according to claim 10, wherein an intensity of the first laser energy is greater than an intensity of the second laser energy.

14. The method according to claim 10, wherein the blade surface extends between a trailing edge and a leading edge of each blade.

15. The method according to claim 10, further including providing a port wherein the laser beam is emitted through a port.

16. The method according to claim 15, wherein the port is located on an outer diffuser of the gas turbine.

17. The method according to claim 15, further including orienting the port such that the laser beam impinges on a row of blades located adjacent an exhaust cylinder section of the gas turbine.

18. A method for detecting at least one locked blade assembly that becomes locked during a turning gear operation for a gas turbine wherein the gas turbine includes a plurality of blade assemblies arranged in rows wherein each blade assembly includes a blade and wherein adjacent blades in a row are separated by a first distance forming a space between adjacent blades to orient each blade in a first position, comprising:
   emitting a laser beam that impinges on a blade surface of each blade in a row of blades located adjacent an exhaust cylinder section of the gas turbine wherein the blade surfaces in the row of blades are substantially equal to each other in size and wherein the laser beam is also transmitted through each space between adjacent blades to impinge on corresponding internal surfaces of the gas turbine;

detecting a first time period in which first laser energy is reflected from each blade surface and a second time period in which second laser energy is reflected from each internal surface and transmitted through each space to provide a plurality of first and second time periods; and detecting whether at least one second time period has increased relative to remaining second time periods wherein the first distance is measured from a first blade that is not deflected from the first position during the turning gear operation and an increase in at least one second time period indicates that a distance between the first blade and an adjacent blade has increased relative to the first distance thereby indicating at least one locked blade assembly.

19. The method according to claim 18, wherein an intensity of the first laser energy is greater than an intensity of the second laser energy.

20. The method according to claim 18, wherein the blade surface extends between a trailing edge and a leading edge of each blade.

* * * * *